United States Patent
Cofer et al.

(10) Patent No.: US 11,179,263 B1
(45) Date of Patent: Nov. 23, 2021

(54) HAND TREMOR REDUCTION DEVICE

(71) Applicants: Savannah Ashley Cofer, Gahanna, OH (US); Alexander LiChen, New Albany, OH (US); Meredith Josephine Schroeder, Worthington, OH (US); Varun Venkat Vallabhaneni, Gahanna, OH (US); Ashton Cameron Cofer, Gahanna, OH (US)

(72) Inventors: Savannah Ashley Cofer, Gahanna, OH (US); Alexander LiChen, New Albany, OH (US); Meredith Josephine Schroeder, Worthington, OH (US); Varun Venkat Vallabhaneni, Gahanna, OH (US); Ashton Cameron Cofer, Gahanna, OH (US)

( * ) Notice: Subject to any disclaimer, the term of this patent is extended or adjusted under 35 U.S.C. 154(b) by 400 days.

(21) Appl. No.: 14/788,782

(22) Filed: Jun. 30, 2015

(51) Int. Cl.
*A61F 5/01* (2006.01)
*A41D 19/00* (2006.01)
*A41D 19/015* (2006.01)

(52) U.S. Cl.
CPC .......... *A61F 5/013* (2013.01); *A41D 19/0013* (2013.01); *A41D 19/01582* (2013.01)

(58) Field of Classification Search
CPC .......... A61F 5/013; A61F 2/583; G06F 3/014; G06F 3/016; A61B 5/0022; A61B 5/225; A61B 5/6806; A61H 1/0288
See application file for complete search history.

(56) References Cited

U.S. PATENT DOCUMENTS

| | | | | |
|---|---|---|---|---|
| 3,944,220 A | * | 3/1976 | Fasano | A63B 21/0552 482/47 |
| 4,719,906 A | * | 1/1988 | DeProspero | A61F 5/013 602/21 |
| 4,781,178 A | * | 11/1988 | Gordon | A61F 5/0118 602/22 |
| 5,156,168 A | * | 10/1992 | Canterna | A61F 5/05866 128/879 |
| 5,527,244 A | * | 6/1996 | Waller | A63B 23/16 482/124 |
| 6,119,271 A | * | 9/2000 | Byon | A63B 21/065 2/161.2 |
| 7,156,819 B2 | * | 1/2007 | Sieller | A61F 5/013 602/21 |
| 7,415,735 B2 | * | 8/2008 | Erickson | A41D 19/01547 2/163 |
| 7,731,633 B1 | * | 6/2010 | Williams | A63B 21/0552 482/148 |
| 8,029,414 B2 | * | 10/2011 | Ingvast | A61H 1/0288 482/4 |
| 10,076,143 B2 | * | 9/2018 | Marriott | A63B 21/0421 |
| 2003/0195093 A1 | * | 10/2003 | White | A63B 21/0552 482/124 |
| 2009/0240184 A1 | * | 9/2009 | Tadman | A61F 5/013 602/22 |
| 2015/0253847 A1 | * | 9/2015 | Harris | G06F 3/017 345/156 |

* cited by examiner

*Primary Examiner* — Ophelia A Hawthorne
(74) *Attorney, Agent, or Firm* — Michael D. Eisenberg

(57) ABSTRACT

Therefore, aspects of some embodiments of the present invention, relates to a device for suppressing essential tremors comprising a glove and wires integrated thereon. The glove is configured to fit on a user's hand. The wires may be attached to the posterior or anterior surface of the glove and configured to supply resistance to movements of the fingers.

13 Claims, 6 Drawing Sheets

HAND TREMOR REDUCTION DEVICE

TECHNICAL FIELD

The present invention, in some embodiments thereof, relates to a non-prescription medical device worn to reduce the effect of essential hand tremors.

BACKGROUND OF THE INVENTION

Essential tremors are one of the most common movement disorders affecting 10 million Americans and 500 million people worldwide. The disorder typically involves tremors in the arms, hands, and fingers. Tremors tend to intensify when one uses the affected muscle. Tremors can range in severity. Patients with severe tremors have difficulty with every day activities. Even patients with mild tremors can find activities that require fine motor activity difficult. The disorder is progressive, increasing in severity over time, in most patients. People with severe tremors have difficulty with tasks such as holding a glass without spilling, eating normally, shaving, and writing legibly.

The cause of essential tremors is not well-understood at present, therefore treatments focus on the effects of the disorder. It is known that tremors occur because of abnormal neural responses from the brain to the flexor and extensor muscles of the hand and forearm. Certain compositions and conditions are known to increase the likelihood of a tremor. Preventative treatments include avoiding caffeine and stress. Maintaining a regular sleep schedule is also recommended. These methods are not always practical or effective depending on the severity of the tremors. Physical therapists recommend using heavier glasses or writing utensils to mitigate the effect of tremors on the object itself. Occasionally patients will self-treat with alcohol, which improves the symptoms, but only temporarily. Furthermore the tremors tend to worsen after the temporary improvement and build a tolerance.

Medicine is sometimes prescribed. Typically the first medicine suggested is a beta blocker such as propranolol. Beta blockers are not appropriate for all patients, especially if they have asthma or heart problems. Additionally beta blockers are not always effective. Anti-epileptic medicines, such as primidone, are also prescribed. Beta blockers and anti-epileptics only work in 40-60% of cases and show only a modest reduction in the amplitude of tremors (typically 20-60%). Both drugs cost approximately $400-$1200 per year. As final recourse in medicine, atypical antipscyhotics, antidepressants, and tranquilizers such as clozapine, mirtazapine, and xanax are used. Some of these drugs may be habit forming or have other adverse side effects. Doctors at the Veterans Administration Hospital in Columbus have indicated that most patients who try Propranolol or Primidone eventually discontinue their use due to their side effects.

On occasion further methods are used such as deep brain stimulation surgery or botulinum toxin injections. Deep brain stimulation tends to be an effective solution in 80-90% of cases, but is both expensive (costs up to $120,000 plus $25,000 every four years for battery replacement) and has surgical risks that many patients are not willing to accept.

BRIEF SUMMARY OF THE INVENTION

There is a need for a non-prescription, non-invasive medical device that allows sufferers of essential tremors to perform a variety of everyday functions without medication or surgery. The present invention relates, in some embodiments thereof, to a wearable medical device that provides mechanical resistance to the extensor carpi radialisbrevis and flexor carpi radialis muscles. No similar devices have been identified in the literature.

While other devices require costly and continuous drug use or surgery, embodiments of the present invention allow users to control their essential tremors mechanically through a safe and cost effective device. Furthermore, they allow interaction with the variety of objects that a user may come in contact with during the course of a regular day rather than restricting usage to certain specialized weighted objects.

In one embodiment of the invention a glove-like device is fitted over a user's hand with wires attached and extending from about the wrist on the back of the hand to about the fingertip along the back of the hand and fingers. While the root cause of essential tremors is unknown at present, it is known that tremors occur because of abnormal neural responses from the brain to the flexor and extensor muscles of the hand and forearm. The invention supplies pressure in specific locations along the hand help to suppress tremors in the muscles that they occur in by providing structure and support. These wires effectively counter the tremors caused in the flexor and extensor muscles. Tests have shown 80% increased success in holding water glasses without spilling. Users who previously could not draw straight lines found that they were capable of that.

The wires, with optimized elastic moduli, have been secured to form fitting gloves to provide the desired mechanical resistance. This has been found to be effective. Embodiments of the invention have been found to reduce the amplitude of tremors by an average of 65%. The invention can also be used to steady hands generally, for uses like enhancing fine motor skills or for a surgeon who needs to improve precision.

Therefore, aspects of some embodiments of the present invention, relates to a device for suppressing essential tremors comprising: a glove and wires. The glove is configured to fit on a user's hand. The wires are attached to the posterior surface of the glove and configured to supply resistance to movements of the fingers.

Variants of the glove may be composed of at least one of pliable leather, pliable synthetic leather, cloth, synthetic fibers, and elastic. Variations of the glove may comprise gaps in the glove configured to allow exposed skin. Variants of the glove contain a fitting piece configured to allow a user to tighten or loosen the device.

In a variant the wires are configured to be placed over the digits of the hands such that they are centered over the digit on the dorsum of the hand, and in the plane defined by the contraction of the digit.

In a variant the wires may be rigid. One example thereof is 18 gauge plastic coated copper wires. The wires may be a plurality of rigid wires configured to extend from about the wrist to about the fingernail of a user's hand.

In another variant the wires are stretchable. Examples of stretchable materials include elastic or rubber bands.

In a variant the wires are attached by holders. Examples of potential materials comprising the holders include: elastic and thread. A typical design may have holders configured to have at least two end loops with at least one middle loop. The end loops have an open end and a closed end and are configured to encase the wire between them. The wire can be sized such that the distance between the closed end loops encases the wire and will cause a slight compression of the wire to hold it with the glove. A middle loop may prevent the wire from moving away from a user during compression.

In variants, the wires cross each other at angles to provide structural support in at least one of the wrist and knuckles.

In yet another variant the device for suppressing essential tremors comprises: a glove, a plurality of wires, gaps in the glove, a fitting piece, and holders. The glove is configured to fit on a user's hand and has a posterior surface. The plurality of wires is attached to the posterior of glove and is configured to supply resistance to movements of the fingers. The gaps in the glove are configured to allow exposed skin. The fitting piece is configured to allow a user to tighten or loosen the device. The holders attach the wires to the device.

The holders in this variant may comprise at least two end loops with at least one middle loop. The end loops have an open end, a closed end, and are configured to encase the wire between them. The wire itself is sized such that the distance between the end loops, when the wire is encased between the closed end loops, will cause a slight compression of the wire to hold it with the glove. The middle loop prevents the wire from moving away from a user during compression. The wires are configured to be placed over the digits of the hands such that they are centered over the digit on the dorsum of the hand, and in the plane defined by the contraction of the digit.

There is a method for suppressing essential tremors by wearing the device.

Various objects, features, aspects, and advantages of the present invention will become more apparent from the following detailed description of preferred embodiments of the invention, along with the accompanying drawings in which like numerals represent like components.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The present invention, in some embodiments thereof, relates to a non-prescription medical device worn to reduce the effect of essential hand tremors. A form fitting glove is equipped with wires to provide a constant opposing force to the periodic vibrations of essential tremors.

In operation, the users put on their gloves and go about their day as usual.

Figure 1:
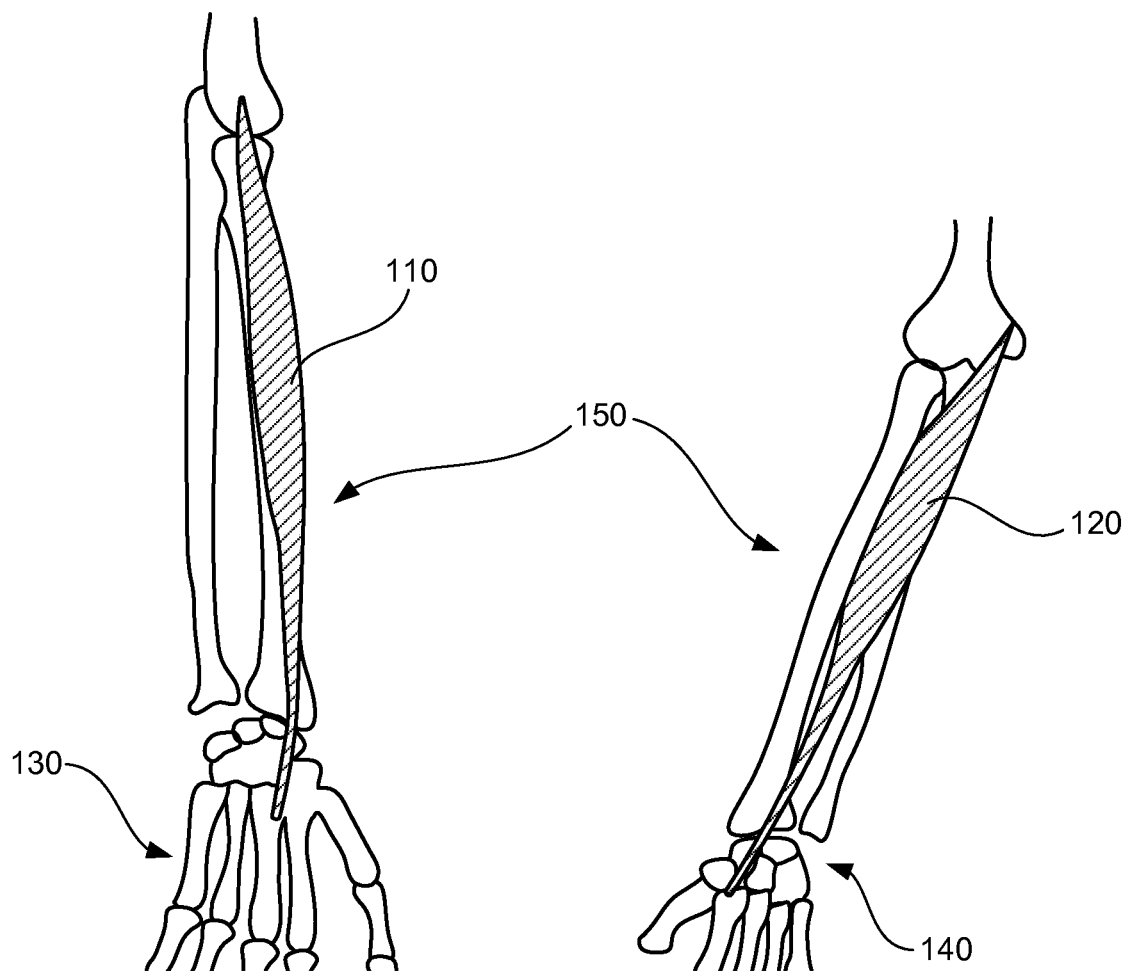
FIG. 1 is a schematic depicting muscles in the arm that the medical device will act upon.

FIG. 1 is a schematic depicting muscles in the arm upon which the medical device will act, but it does not display the medical device itself. The extensor carpi radialis brevis 110 and flexor carpi radialis 120 muscles have both been found to be affected in patients with essential tremors. The flexor carpi radialis 120 is a muscle of the forearm 150 that flexes and abducts the hand 130, and extensor carpi radialis brevis 110 is a muscle in the forearm 150 that acts to extend and abduct the wrist 140. The muscles 110 and 120 of the forearm 150 extend into the hand 130. When the device is on the hand it supplies resistance to the hand and finger movements caused by these muscles 110 and 120.

Figure 2:
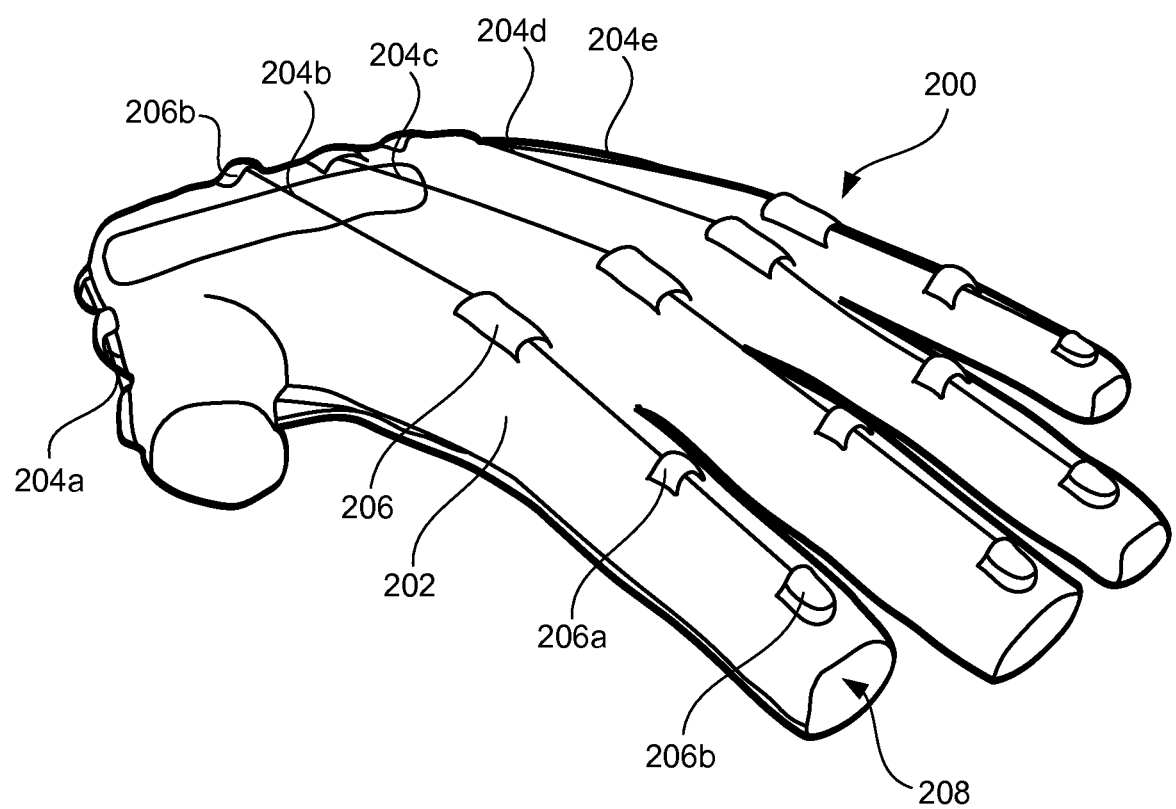
FIG. 2 is a three dimensional schematic of an embodiment of the medical device.

FIG. 2 is a three dimensional schematic of an embodiment of the medical device. The medical device 200 comprises a glove 202 and wires 204 with the wires 204 affixed to the glove 202 by holders 206. The holders 206 may come in several forms wherein the wires 204 are either almost completely exposed or completely encased within the medical device 200. In this embodiment the wires 204 are generally not enclosed and held in place by about four holders 206 that conform the wires 204 to the glove 202. In this embodiment the holders 206 are middle loops 206a between two end loops 206b, the end loops 206b having an open end and a closed end each with the wire 204 held between them. The wire 204 is sized such that when placed between the end loops 206b the distance between the closed end of the end loops 206b will cause wire 204 to be tight-fitting and hold it with the glove with the middle loops 206a holding the wire 204 parallel to the plane of the hand. As described above, while in this embodiment the holders 206 are composed of distinct and separate loops, a holder 206 may contain the elements of these loops while the loops are connected and therefor contain the wire 204 entirely.

In this embodiment there are a total of five wires indicated as 204*a-e*. Each of these runs along the posterior surface of the fingers, thumb through pinky respectively, from about the wrist. Depending on the specific embodiment the number and organization of the wires 204 may alter, but generally the wires 204 will run from about the wrist and end at about the nail bed of each finger. The wires 204 are configured to be placed over the digits of the hands such that they are centered over the digit on the dorsum of the hand, and in the plane defined by the contraction of the digit. In another variant, the wires may run along the anterior surface of the fingers.

The device may have gaps 208 that allow for skin exposure. The gaps 208 in this embodiment leave the fingertips exposed which allows a user to freedom use have maximum touch and dexterity.

Figure 3:
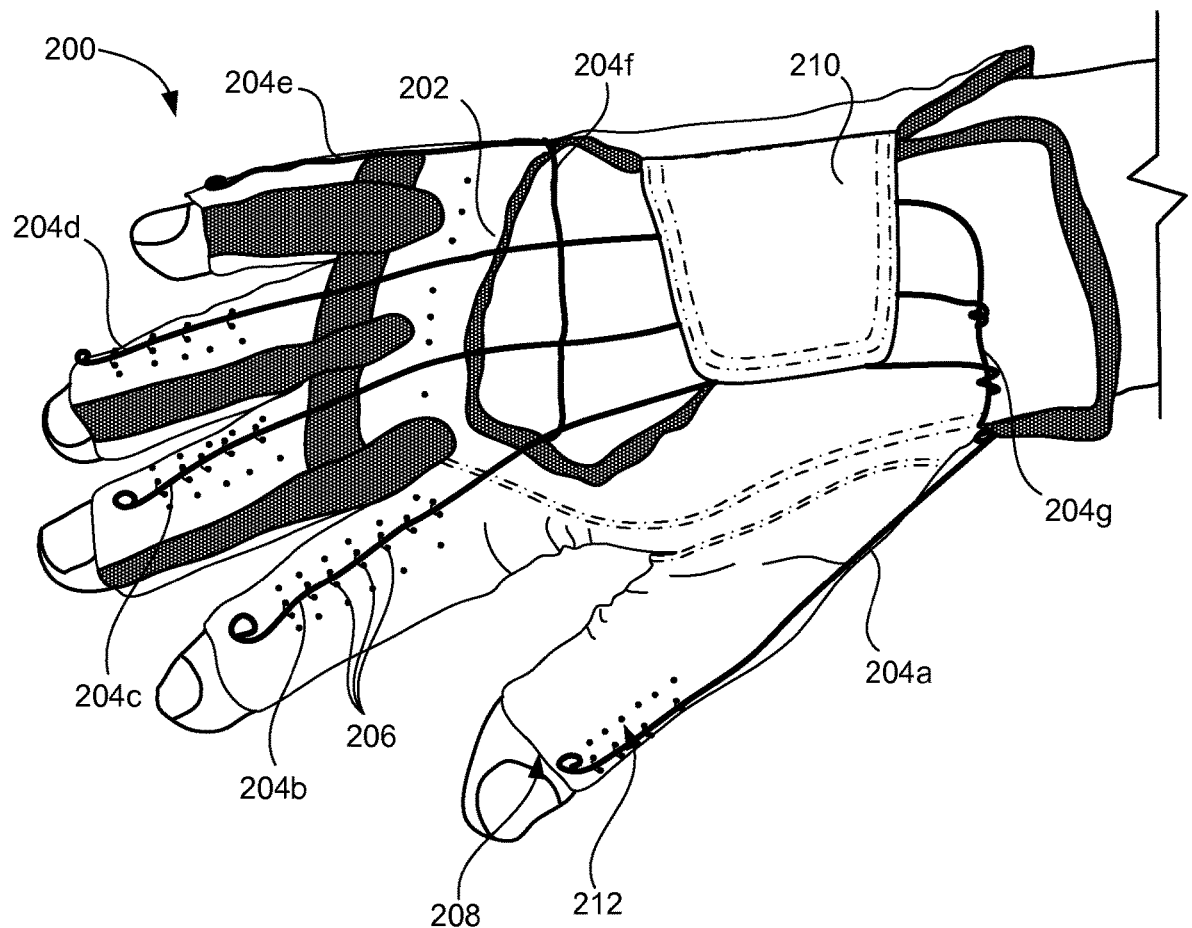
FIG. 3 is a schematic of an embodiment of the medical device in use.

FIG. 3 is a schematic of an embodiment of the medical device in use. In this embodiment the wires 204 have an alternate arrangement wherein 204f and 204g provide stability and structure to the other wires along with holders 206. The holders 206 in this embodiment are smaller and occur with greater frequency than in FIG. 2. FIG. 2 contains optional variations. In addition to the alternate wire 204 and holder arrangements, the glove has a fitting piece 210 that allows it to be fitted to several differently sized hands, and small holes 212 to allow the skin to breath.

Figure 4:
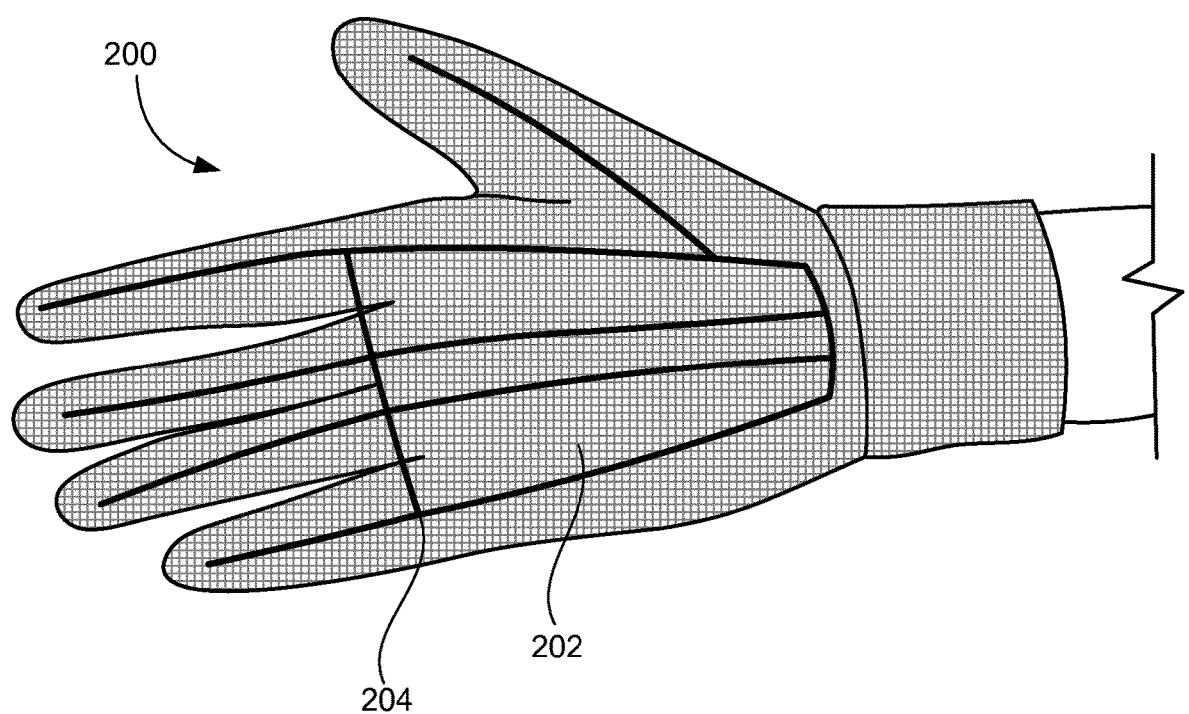
FIGS. 4, 5 and 6 are schematics of non-exhaustive variations on the medical device.
Figure 5:
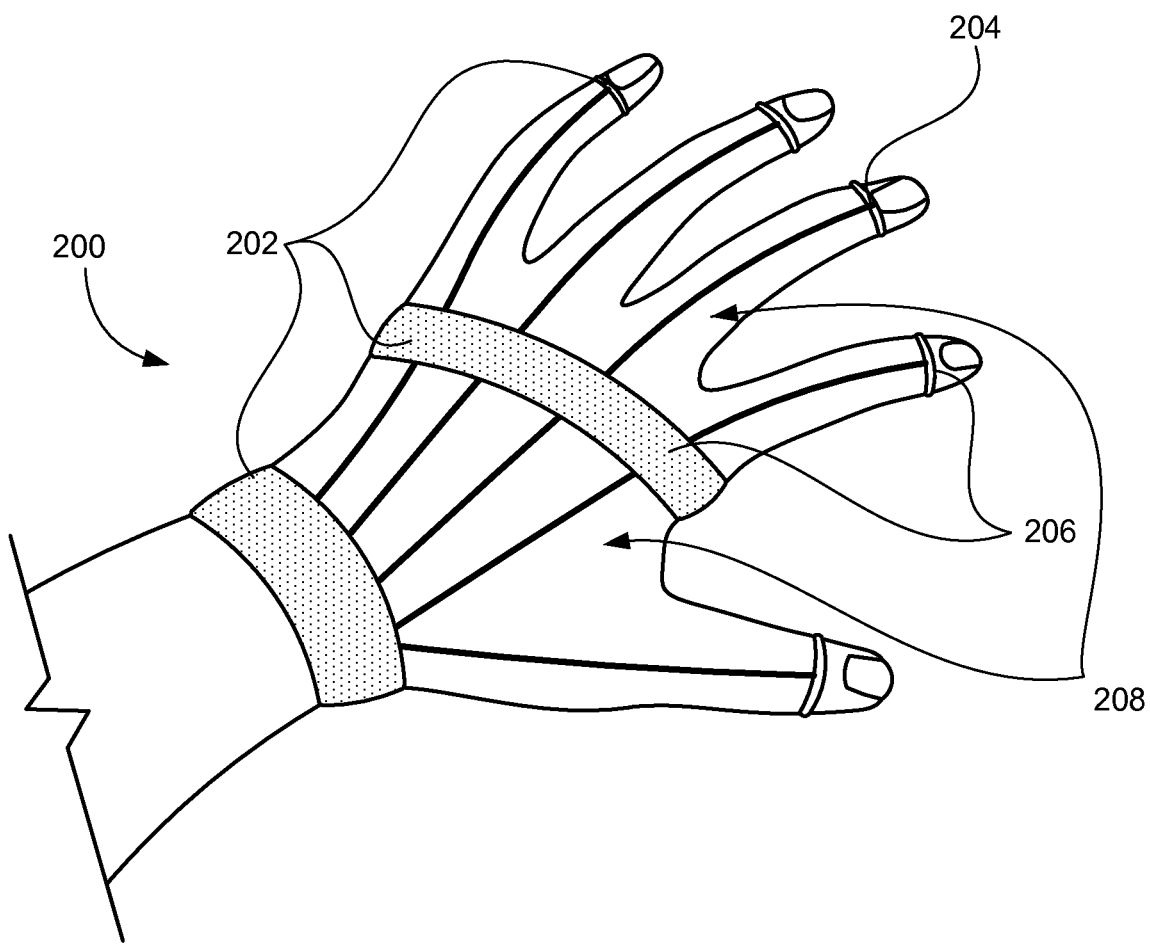
Figure 6:
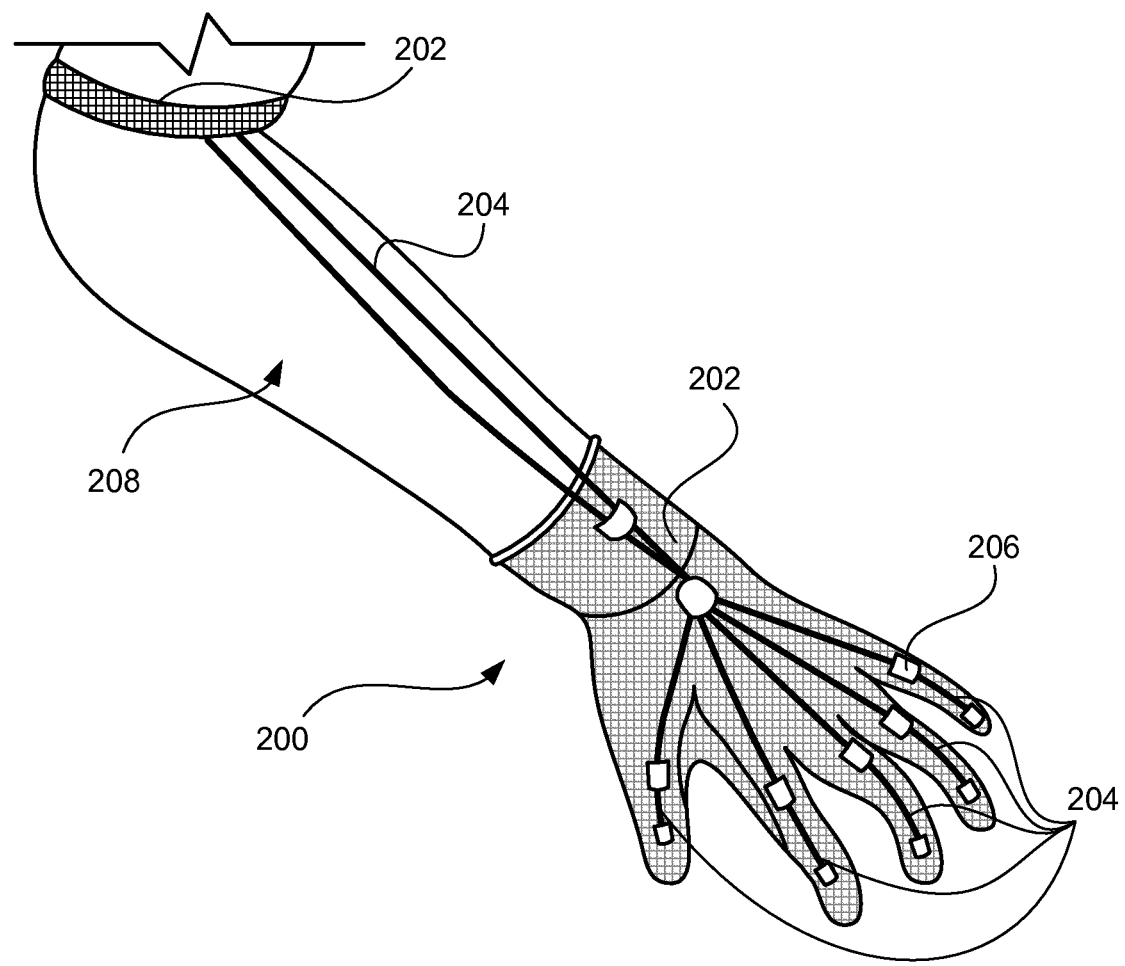

FIGS. 4, 5 and 6 are schematics of non-exhaustive variations on embodiments of the medical device. FIG. 4 is a simple embodiment with a glove 202 and wires 204 depicted with the wires 204 having an arrangement similar to that in FIG. 3. In an embodiment such as this, the wires 204 could be enclosed completely within the glove 202. FIGS. 5 and 6 have wires 204 that illustrate an alternative embodiment in which the wires 204 are elastic bands. In both FIGS. 5 and 6, the wires 204 may be created from materials that stretch, like elastic, or are rigid. These alternate options provide different styles of support. The wires provide resistance to the actions of hand tremors through a force of resistance that increases as the elastic bands are stretched. Rigid wires provide a constant force of resistance against tremors.

FIG. 5 is an alternate embodiment of attaching the wires 204 to the device. FIG. 5 is an open design where the glove 202 is designed with large gaps 208 between the wrist portion of the glove, the knuckle portion of the glove, and the fingertip portion of the glove. The elastic bands 204 are arranged in a similar fashion as in FIG. 2 with holders 206 providing support at the wrist, knuckles, and finger tips. In this embodiment, individual elastic band 204 can be attached to rings acting as a glove 202 that are secured around each fingertip. Different embodiments have differing benefits. Similarly different embodiments may be preferred by different users, during different times of year, or in different climates. This attachment method may improve air-flow. The durability of the device may improve. Elastic bands may have less of a tendency to become detached. In FIG. 5, the elastic bands 204 are also attached to bands 202 that run across the back of the hands and wrist, respectively. This attachment method may also provide improved durability of the device.

FIG. 6 provides an alternate glove 202 and elastic band 204 design wherein the glove 202 is fitted to the user's hand and extends up past the user's elbow with gap 208 between the two. The elastic bands 204 also extend past the elbow, extend further up the forearm, and attach to a band to secure them. This embodiment may provide additional resistance to further reduce the magnitude of tremors.

Because gaps 208 may be of several sizes, the portion of the glove 202 that covers the hand can be greatly reduced such that glove 202 refers generally to the portion of the device 200 that allows the device 200 to be secured to the user. The method of attachment of the wires 204 may greatly change depending on a specific embodiment such that the wires 204 may have holders 206 alternate configurations as FIGS. 2 and 3. The wires 204 may also be attached through an adhesive or incorporated internally within the glove 202.

In developing the device 200, it may be prepared for a specific individual or designed for individuals generally. A glove 202 is first sized for the user. Next pieces of plastic coated copper wire 204 are cut to size. Five wires 204 extend along each finger and terminate at wrist as shown back in FIG. 2. A sixth wire, such as 204f in FIG. 3, may be held generally perpendicular at the knuckles and attached to the wires that run along each finger to provide additional stability. The wires 204 typically either join together at the wrist, as in FIG. 6 or may be secured separately by holders 206, or an additional wire such as 204g. All loose ends of the wires 204 should be secured and tucked in for safety reasons.

In one variation of the invention the device 200 uses 18 gauge plastic coated copper wires 204 sewn along each linger of a fitted and flexible leather glove 202. In operation the wires 204 provide constant resistance to the small movements of the extensor carpi radialis brevis and flexor carpi radialis muscles that are the primary sources of hand tremors. The glove 202 may be lightweight and comfortable, and the fingertips may be exposed through gaps 208 in order to allow the user to have maximum touch and dexterity. Depending on the individual's severity of hand tremors, the strength, gauge, or type of the wire 204 can be altered. For many patients, it was found that 18 gauge copper with an elastic modulus of 125 GPa provided a beneficial balance between resistance and tactility. When measured along three different axes, the medical device 202 has been shown to significantly reduce tremor amplitude in all three.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to achieve the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A device for suppressing essential tremors comprising:
   a glove, configured to fit on a user's hand, having a posterior surface associated with a dorsum of the hand;
   a plurality of wires, not having a shape memory, attached to the posterior of said glove and configured to supply resistance to movements of the fingers;
   wherein the wires are configured to be completely enclosed by the glove;
   wherein the wires are configured to extend from a dorsum of a palm, over respective knuckles, to about respective fingernails of a user's hand, when the glove is worn on the user's hand;
   wherein the plurality of wires are rigid to provide a constant force of resistance against tremors,
   wherein at least one of the wires is attached to the glove by a plurality of holders at different locations along the at least one of the wires
   wherein the plurality of holders for the at least one wire comprise:
      at least two end loops with at least one middle loop;
      each end loop having an open end and a closed end and the end loops are configured to encase a respective wire between the end loops;
   wherein the respective wire is sized such that a distance between the corresponding end loops, when the at least one wire is encased between the closed ends of the end loops, causes a slight compression of the wire to hold it with the glove; and
   wherein the middle loop is configured for preventing the wire from moving away from a user during compression.

2. The device of claim 1, wherein the wires are configured to be placed over the digits of the hands such that they are centered over the digit on the dorsum of the hand, and in the plane defined by the contraction of the digit.

3. The device of claim 2, wherein the wires are less than or equal to 18 gauge plastic coated copper wires.

4. The device of claim 2, wherein the wires are stretchable.

5. The device of claim 1, wherein the wires are less than or equal to 18 gauge.

6. The device of claim 5, wherein the wires are copper.

7. The device of claim 1, further comprising gaps in the glove configured to allow exposed skin.

8. The device of claim 1, further comprising a fitting piece configured to allow a user to tighten or loosen the device.

9. The device of claim 1, wherein the holders are elastic.

10. The device of claim 1, wherein the holders are thread.

11. A device for suppressing essential tremors comprising:
    a glove, configured to fit on a user's hand, having a posterior surface associated with a dorsum of the hand,
    a plurality of wires, not having a shape memory, attached to the posterior of said glove and configured to supply resistance to movements of the fingers;
    wherein the wires are configured to extend from a dorsum of a palm, over respective knuckles, to about respective fingernails of a user's hand, when the glove is worn of the user's hand;
    wherein the plurality of wires are rigid to provide a constant force of resistance against tremors;
    the device further comprising crossing wires located over a dorsum of a palm area of the glove, the crossing wires crossing at least some of the plurality of wires at angles, and wherein at least one of the crossing wires extends across the glove configured to be positioned from the ulnar side to the radial side of the user's hand.

12. The device of claim 11, wherein the crossing wires are attached to the plurality of wires at points where the crossing wires cross the plurality of wires.

13. A method for suppressing essential tremors, comprising:
    inserting a user's hand into a device having a glove;
    supplying a constant force of resistance to movements of a user's fingers via a plurality of wires attached to a posterior surface of the glove, associated with a dorsum of the hand, such that the wires are configured to extend from a dorsum of a palm, over respective knuckles, to about respective fingernails of the user's hand when the glove is worn on the user's hand;
    exposing areas of a user's skin via a plurality of gaps disposed in the glove;
    changing a size of the glove via a fitting piece configured to loosen or tighten the glove; and attaching at least one of the wires to the device via a plurality of holders at different locations along the at least one of the wires;
wherein the plurality of holders for the at least one wire comprise:
 at least two end loops with at least one middle loop;
 each end loop having an open end and a closed end and the end loops are configured to encase a respective wire between the end loops;
wherein the respective wire is sized such that a distance between the corresponding end loops, when the at least one wire is encased between the closed ends of the end loops, causes a slight compression of the wire to hold it with the glove; and
wherein the middle loop is configured for preventing the wire from moving away from a user during compression.

* * * * *